United States Patent [19]

Walch et al.

[11] Patent Number: 4,557,955
[45] Date of Patent: Dec. 10, 1985

[54] SHAPED ARTICLES WHICH ARE COMPOSED OF A COPOLYMER CONTAINING FLUORINE GROUPS AND WHICH ARE SELECTIVELY PERMEABLE TO LIQUIDS AND GASES AND ARE SIMULTANEOUSLY OLEOPHOBIC AND OLEOPHILIC

[75] Inventors: Axel Walch, Frankfurt; Walter Seifried; Wolfgang Michel, both of Wiesbaden; Jürgen Kuhls, Burghausen; Jürgen Wildhardt, Huenstetten, all of Fed. Rep. of Germany

[73] Assignee: Hoechst Aktiengesellschaft, Frankfurt am Main, Fed. Rep. of Germany

[21] Appl. No.: 402,265

[22] Filed: Jul. 27, 1982

[30] Foreign Application Priority Data

Jul. 28, 1981 [DE] Fed. Rep. of Germany ....... 3129744

[51] Int. Cl.$^4$ ............................................. B01D 39/16
[52] U.S. Cl. ..................... 428/35; 428/422; 55/522; 428/913; 430/18; 55/528; 430/20; 430/138; 55/DIG. 42; 430/348; 430/496; 204/296; 204/301; 210/500.2; 210/510.1; 210/927; 264/41; 264/48; 264/176 F; 264/178 F; 264/178 R; 264/209.1; 264/209.3; 264/210.1; 424/19; 424/22; 424/27; 424/DIG. 7; 427/55; 427/244; 428/305.5; 428/315.5; 428/315.7; 428/316.6; 428/320.6; 428/320.8; 428/321.5; 428/322.7; 428/398; 428/401
[58] Field of Search ......................... 210/500.2, 510.1; 55/522, 528, DIG. 42; 424/DIG. 7; 427/55, 244; 428/315.5, 315.7, 316.6, 398, 401, 422, 913, 35; 264/41, 48, 176 F, 178 F, 178 R, 209.1, 209.3, 210.1; 430/20, 138, 496

[56] References Cited

U.S. PATENT DOCUMENTS

| 2,468,664 | 4/1949 | Hanford et al. | |
|---|---|---|---|
| 3,445,434 | 5/1969 | Stilmer . | |
| 3,615,024 | 10/1971 | Michaels . | |
| 4,049,589 | 9/1977 | Sakane . | |
| 4,220,543 | 9/1980 | Yamashita | 210/500.2 |
| 4,238,571 | 12/1980 | Mano et al. | 521/62 |
| 4,248,913 | 2/1981 | Jakabhazy et al. | 210/500.2 |
| 4,318,785 | 3/1982 | Gunjima et al. | 210/500.2 |
| 4,362,677 | 12/1982 | Yamashita et al. | 210/500.2 |
| 4,376,140 | 3/1983 | Kimoto et al. | 210/500.2 |
| 4,377,010 | 3/1983 | Fydelor et al. | 210/500.2 |
| 4,384,047 | 5/1983 | Benginger et al. | 210/500.2 |

FOREIGN PATENT DOCUMENTS 0012557 6/1980 European Pat. Off. .

OTHER PUBLICATIONS

European Search Report.

Primary Examiner—James C. Cannon
Attorney, Agent, or Firm—Schwartz, Jeffery, Schwaab, Mack, Blumenthal & Evans

[57] ABSTRACT

The invention relates to films and tubular structures which are selectively permeable to liquids and gases which are based on a copolymer composed of a copolymerized fluorinated olefin, copolymerized vinyl acetate and, optionally, a copolymerized olefin. It is possible for the acetate groups of the copolymer to have been saponified to form OH groups. The films or tubular structures have in each case an inherent, latent capacity for modifying their structure and are at the same time oleophobic and oleophilic. The invention also embraces processes for the preparation of the shaped articles described and processes for modifying their structure. The invention also relates to the use of shaped articles according to the invention.

35 Claims, 2 Drawing Figures

FIGURE I
FIGURE II
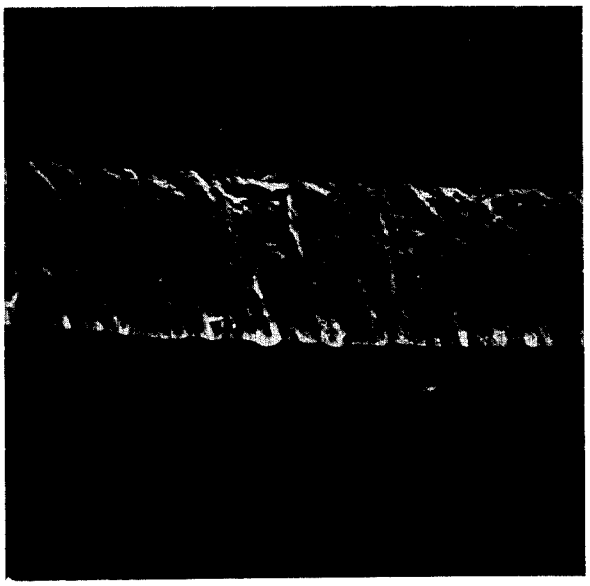

SHAPED ARTICLES WHICH ARE COMPOSED OF A COPOLYMER CONTAINING FLUORINE GROUPS AND WHICH ARE SELECTIVELY PERMEABLE TO LIQUIDS AND GASES AND ARE SIMULTANEOUSLY OLEOPHOBIC AND OLEOPHILIC

BACKGROUND OF THE INVENTION

The present invention relates to shaped articles which are composed of a synthetic copolymer containing fluorine groups and which, in their original state, are permeable to liquids and gases and are simultaneously oleophobic and oleophilic, and also to the use of shaped articles of this type. The invention also relates to processes for the preparation of these shaped articles and to processes for modifying their structure. The invention also relates to the use of the shaped articles.

Within the scope of the description of the present invention and of the claims, the term "shaped articles" is intended to embrace films and tubular structures, such as tubes and hollow fibers (capillaries). In accordance with the definition, the term "shaped articles" also embraces coatings.

Open-pore, microporous plastic films are known, for example, those composed of polyamide, polysulfone or polyvinylidene fluoride (U.S. Pat. No. 3,615,024), which are prepared in accordance with the so-called phase inversion process by casting a solution of a plastic to form a liquid film and coagulating the plastic dissolved in this solution to form the above microporous film of stable shape.

Open-pore films which are prepared by mixing polyvinylidene fluoride with polyvinyl acetate are also suggested in European Patent Application No. 0,012,557. Only when the film is finished is it subsequently converted by saponification into a mixture containing polyvinyl alcohol. Copolymers of tetrafluoroethylene and vinyl acetate or vinyl alcohol, which are hydrophilic/hydrophobic without further treatment, have hitherto not yet been employed as selectively permeable films.

SUMMARY OF THE INVENTION

It is therefore an object of the present invention to provide shaped articles which, because of the qualitative and quantitative chemical structure of the copolymer of which they are formed, have the property of being at the same time oleophobic and oleophilic.

It is also an object of the invention to provide such shaped articles which are compatible with a very wide variety of constituents with which they are in contact and which have a permeability to liquids and gases which can be adjusted in a variable manner within a wide field.

Another object of the invention is to provide shaped articles which are resistant to corrosive chemical agents and can be dried with or without plasticizers without their pattern of properties being altered and can be remoistened extremely rapidly with different media.

A still further object of the invention is to provide a process for preparing the shaped articles according to the invention.

Another object of the invention resides in providing a process for converting the shaped article of the invention so as to modify its structure.

Finally, it is also an object of the invention to provide several improved articles of manufacture utilizing the shaped articles of the invention, including improved filter membranes, envelopes for containing chemical media, information carriers and analytical and/or diagnostic devices.

In accomplishing the foregoing objects, there has been provided in accordance with one aspect of the present invention a shaped article which is selectively permeable to liquids and gases, comprising a copolymer containing fluorine groups and which is comprised of at least 50% by weight of a copolymer which is comprised of from about 20 to 80%, preferably 30 to 70% by weight, relative to the total weight of the copolymer, of a copolymerized fluorinated olefin, from about 0 to 40%, preferably 0 to 20% by weight, relative to the total weight of the copolymer, of a copolymerized olefin and from about 80 to 20%, preferably 70 to 30% by weight, relative to the total weight of the copolymer, of copolymerized vinly acetate, wherein optionally at least about 5% by weight of the total acetate groups, and preferably at least about 80% thereof, have been converted to OH groups by saponification of the copolymer.

In one embodiment the shaped article comprises a film or hollow fibers having effective pores of a diameter within the range of from about 0.002 to 10 $\mu$m, preferably from about 0.002 to 0.05 $\mu$m, and through which liquies and gases can flow, and which has an inherent, latent capacity for modifying its structure until the limiting case of substantial physical homogeneity of the film is reached.

In another embodiment, the shaped article comprises a film or hollow fibers having effective pores of a diameter within the range from about 0.05 to 10 $\mu$m.

In accordance with another aspect of the present invention, there has been provided a process for the preparation of a shaped article as described above, comprising the steps of providing a liquid solution containing, as the dissolved component, 1 to 50% by weight, relative to the total weight of the solution, of a polymer comprising at least 50% by weight, relative to the total weight of the dissolved components of the solution, of a copolymer which is comprised of 20 to 80% by weight, relative to the total weight of the copolymer of a copolymerized fluorinated olefin, from about 0 to 40% by weight, relative to its total weight, of a copolymerized olefin and from about 80 to 20% by weight, relative to its total weight, of copolymerized vinyl acetate, wherein at least 5 % by weight of the acetate groups in the copolymer, relative to the total quantity thereof in the copolymer, have been converted into OH groups by saponification of the copolymer; forming a shaped article, preferably a film or hollow fibers from the liquid solution; and coagulating the copolymer by treating the shaped article with a precipitation liquid to form a shaped article having a porous structure and a stable shape.

According to still another aspect of the invention, there has been provided a process for modifying the structure of a shaped article as described above, comprising the steps of subjecting a shaped article to the action of an agent which is capable of rendering the structure of the copolymer of which the shaped article is formed physically or optically homogeneous, wherein the agent is heat, a chemical agent in the gaseous or liquid state, and/or pressure applied separately or in combination.

According to still further aspects of the present invention, there have been provided a filtration device useful as an ultra-filter or hemo-filter or for separating or purifying dispersions, emulsions and dissolved macromolecules; a membrane filter useful for the separation of coarsely dispersed aqueous and gaseous systems, for separating particular impurities from solutions for infusions, for separating cellular constituents from fermentation solutions, for separating bacteria or viruses from solutions or gases (sterile filters) or for separating very fine particles or aerosols from gases; a reservoir for containing low or high-molecular weight substances; an information carrier, comprising a molded article as described above, being structurally converted in at least certain preselected areas, whereby the preselected areas represent information transferred by the molded article; and a device for use in analytical and/or diagnostic processes, comprising such a molded article containing in its effective pores an analytical or diagnostic agent.

The shaped articles which are selectively permeable to liquids and gases are thus not only compatible with both oleophilic and oleophobic fluids, but can, in addition, be provided either with a very open-pore structure or with a narrow-pore structure by means of simple variants during their preparation.

Further objects, features and advantages of the present invention will become apparent from the detailed description of preferred embodiments which follows, when considered with the attached figures of drawing.

BRIEF DESCRIPTION OF THE DRAWINGS

In the drawings:

FIG. I is a photograph, at a magnification of 3,000, of a cross section of a film according to the first variant of the subject of the invention; and FIG. II is a photograph of a film having a virtually homogeneous physical structure, which has been prepared by structural modification of a film shown in FIG. I.

DETAILED DESCRIPTION OF PREFERRED EMBODIMENTS

The film according to the invention or the wall of the tubular structure according to the invention is, in its original form, permeable to liquids and gases which in each case do not incipiently dissolve or attack the copolymer forming the film or the tubular structure. The term film or tubular structure in its original form is understood to mean in each case a film or a tubular structure which has not been subjected after its preparation to a treatment by means of which it becomes permeable to flowing liquids or gases.

In terms of chemical composition, the shaped article according to the invention comprises at least 50% by weight of a film-forming synthetic copolymer (1) which is composed of 20 to 80% by weight, relative to the total weight thereof, of a copolymerized fluorinated olefin, preferably copolymerized fluorinated ethylene or copolymerized fluorinated propylene, but particularly of copolymerized perfluorinated ethylene, of to 40% by weight, relative to the total weight of the copolymer, of a copolymerized olefin, preferably copolymerized ethylene or copolymerized propylene, and of 80 to 20% by weight, relative to the total weight of the copolymer, of copolymerized vinyl acetate. In accordance with the definitions, copolymer is also to be understood as meaning block copolymers or mixtures thereof. The shaped article can contain up to 50% by weight, relative to its total weight, of polymers which differ from the above-described copolymers in their qualitative chemical composition, which are present to the extent of at least 50% in the shaped article. The shaped article can, for example, comprise at least 50% by weight of the copolymer described and a total of up to 50% by weight of polyvinylidene fluoride, polar polyolefins, silicones or mixtures of these polymers.

The shaped article can also comprise at least 50% by weight of a copolymer which is composed of 20 to 80% by weight, relative to the total weight thereof, of a copolymerized fluorinated olefin, preferably copolymerized fluorinated ethylene or copolymerized fluorinated propylene, but particularly copolymerized perfluorinated ethylene, of 0 to 40% by weight, relative to the total weight of the polymer, of a copolymerized olefin, preferably copolymerized ethylene or copolymerized propylene, and of 80 to 20% by weight, relative to the total weight of the copolymer, of copolymerized vinyl acetate, wherein at least 5% by weight, preferably more than 80% by weight, of the acetate groups in the copolymer, relative to the total amount thereof in the latter, have been converted by saponification into OH groups, after the comonomers described have been copolymerized to give the copolymer. It is also possible to crosslink the copolymer via its functional groups, either with itself, with polymeric admixtures or with multifunctional agents (for example, polyisocyanates).

The shaped article preferably comprises at least 50 % by weight of a copolymer (2) which is composed of 30 to 70% by weight, relative to its total weight, of copolymerized tetrafluoroethylene, of 0 to 20% by weight, relative to the total weight of the copolymer, of copolymerized ethylene and of 70 to 30% by weight, relative to the total weight of the copolymer, of copolymerized vinly acetate.

The shaped article can also comprise at least 50% by weight of a copolymer which is compsed of 30 to 70% by weight, relative to its total weight, of copolymerized tetrafluoroethylene, of 0 to 20% by weight, relative to the total weight of the copolymer, of copolymerized ethylene and of 70 to 30% by weight, relative to the total weight of the copolymer, of copolymerized vinly acetate, wherein more than 5% by weight, preferably more than 80% by weight, of the total quantity of acetate groups present in the said copolymer, relative to their total weight, have been converted into OH groups by saponification after the comonomers described have been copolymerized to give the said copolymer.

The shaped article advantageously contains, for example, a copolymer (3) which comprises 45% by weight of copolymerized tetrafluoroethylene, 7% by weight of copolymerized ethylene and 48% by weight of copolymerized vinly acetate, wherein more than 80% of the acetate groups of the copolymer have been saponified to give OH groups after the copolymer has been prepared.

Another shaped article contains, for for example, a copolymer (4) which is composed of 58% by weight of copolymerized tetrafluoroethylene, of 7% by weight of copolymerized ethylene and of 35% by weight of copolymerized vinyl acetate, wherein more than 80% of the acetate groups of the copolymer have been saponified to give OH groups after the copolymer has been prepared.

A particular shaped article contains, for example, a two-component copolymer (5) which is composed of 62% by weight, relative to the total weight of the copolymer, of copolymerized tetrafluoroethylene and of 38% by weight of copolymerized vinyl acetate, wherein more than 80% of the acetate groups of the copolymer have been converted by saponification into OH groups after the polymer has been prepared.

The percentage figures relating to quantities of designated copolymerized comonomers present in the exemplary copolymers are in each case subject to the proviso that their total sum is 100%. Copolymers of the chenical composition mentioned can be prepared by processes which are familiar to those skilled in the art (see, e.g., U.S. Pat. Nos. 3,445,434 and 2,468,664). The copolymers indicated above are not, per se, the subject of the present invention.

As a result of the chemical composition of the copolymer of which the shaped article is composed, the shaped article within the polymer chains of which it is composed is at the same time oleophobic and oleophilic and is also stable in corrosive media.

In each case, the film according to the invention or the wall of the tubular structure according to the invention advantageously has a thickness within the range from about 0.5 to 800 μm. The film can be self-supporting or can be situated on a supporting sheet-like structure, for example, a stretch-oriented film of polyester or a film of unplasticized polyvinyl chloride.

In a first embodiment or first variant of the invention, the film, or the wall of the tubular structure, according to the invention has an open-pore structure having pores with an effective diameter within the range from about 0.002 to 10 μm.

In this embodiment, the film, or the wall of the tubular structure, permits the flow of liquids, which means that the passage of the latter takes place through the film or through the wall of the tubular structure, in each case via communicating pores. In the case of liquids, molecules dissolved therein are then retained by the film or by the wall of the tubular structure, if these molecules are larger than the pores in the film or in the wall of the tubular structure.

In accordance with the second embodiment of the shaped article according to the invention (the second variant of the invention), this shaped article has a virtually homogeneous physical structure. The statement that the shaped article has a virtually homogeneous physical structure is intended to mean, in terms of definition, that its content of free, light-refracting pores is negligibly low.

In the case of the second variant of the invention, liquids and gases can only pass through the film or the wall of the tubular structure as a result of diffusion. In the course of this, molecules which, because of their molecular size or their solubility, are not capable of diffusing through the film or the wall of the tubular structure, are in each case retained by the latter.

In the case of the first variant of the invention, a film or a tubular structure, particularly in the form of hollow fibers (capillaries) having in each case pores of an effective diameter within the range from about 0.05 to 10 μm, is particularly suitable for use as a membrane filter for the separation of coarsely dispersed aqueous and gaseous systems, for example, for removing formed elements from blood (plasmapheresis), for separating particulate impurities from solutions for infusions, for separating bacteria or viruses from solutions or gases (sterile filters) or for separating very fine particles or aerosols from gases.

Films or hollow fibers of the first variant of the invention having pores with an effective diameter within the range from about 0.002 to 0.05 μm, can be used advantageously, for example, as ultra-filters or hemo-filters or for the separation or purification of dispersions, emulsions and dissolved macromolecules, for example, for the separation of milk/whey or the constituents of blood (artificial kidneys). By virtue of their biological acceptibility and their stability, the said films are also suitable as permeable coatings or media for the uptake and subsequent release of, for example, therapeutic agents, catalysts or other active compounds and substances, for example, the liberation of insulin from implanted cell cultures encased in a membrane.

Shaped articles of the first variant of the invention can be dried after moistening and can be reused thereafter. Their pattern of properties is not changed by the drying process, but they can also be dried after the application of a plasticizer (for example, glycerol).

Shaped articles of the first variant of the invention are characterized by an inherent, latent convertibility of their structure. They are suitable as intermediate products for the preparation of shaped articles which are virtually homogeneous physically, into which they can be converted by a process which modifies their structure.

The hollow fibers described can be used in a clustered form as a unit of a filter element.

Shaped articles according to the invention can be prepared, for example, by coagulating a liquid solution which contains 1 to 50 % by weight, preferably 5 to 25 % by weight, of polymer, relative to the total weight of the solution, the dissolved constituent comprising at least 50 % by weight of one of the copolymers described above. The solvent of the solution can be, for example, dimethylformamide, N-methylpyrrolidone, dimethyl sulfoxide, dimethylacetamide, an aliphatic alcohol, acetone or tetrahydrofuran. The solution is squeezed out in the form of a liquid film from a straight die slot aperture or in the form of liquid hollow fibers from an annular die orifice and is injected into a precipitation liquid. It is also possible, for example, to interpose a dwell time in the atmosphere before the liquid enters the precipitation bath. The copolymer dissolved in the soltuion is insoluble in the precipitation liquid, but the solvent is soluble. The precipitation liquid used is, for example, water.

In its action (which depends, for example, on the temperature of the precipitation bath) on the liquid film or on the liquid hollow fiber, the precipitation liquid coagulates the copolymer contained in the latter with the formation, from the copolymer described, of a film of stable shape or of a hollow fiber of stable shape, which has the selectively permeable structure indicated. The film or the hollow fiber is then freed from excess liquid by drying, or the precipitation liquid is replaced by another liquid (for example, glycerol).

A film according to the invention can also be prepared by applying a liquid layer composed of the copolymer solution indicated above to the surface of a supporting film of stable shape, for example, in the form of a metal band, then allowing a precipitation liquid to act on the liquid layer located on the supporting film and stripping off, from the supporting film, the selectively permeable film thus formed, consisting of the copolymer indicated.

If the supporting film used is, for example, a stretch-oriented polyester film or a rigid PVC film, the supporting film having, for example, a thickness within the range from about 50 to 100 μm and the procedure being carried out in other respects as indicated above, after the copolymer film has been formed on the surface of the supporting film, the two-layer laminate can be used according to the invention after the film has been dried.

The preparation of films having pores of an effective size within the range from about 0.05 to 10 μm can be effected, for example, by preparing a 13 percent by weight solution of the copolymer (designated (5) above) in N-methylpyrrolidone, applying the solution as a coating to a plate of glass by means of a 100 μm doctor blade, and after a dwell time of 4 seconds in the atmosphere (at 21° C.), coagulating the polymer layer for 20 minutes in water (at 16°).

Films which have pores of an effective size within the range from about 0.002 to 0.005 μm can, for example, be prepared by dissolving 15 percent by weight of the copolymer (according to (3) above) with 4 percent by weight of polyvinylpyrrolidone in N-methylpyrrolidone/tetrahydrofuran (5:1), applying the solution as a coating to a plate of glass by means of a 100 μm doctor blade, and after a dwell time of 20 seconds in the atmosphere (at 21° C.), coagulating the polymer layer for 30 minutes in water (at 16° C.).

The preparation of hollow fibers in which the walls have pores of the above-mentioned size is effected under the conditions indicated above, but with the modification that the polymer solution is injected into the precipitating agent through an annular die orifice. Shaped articles, in particular films, according to the second variant of the invention can also be prepared, for example, by subjecting a shaped article prepared as indicated, for example, a film, to one of the physical or chemical processes mentioned below or to a combination of both. This can be done in a further process stage, for example:

1. The action of heat on the film. Depending on the chemical composition of the film or of the copolymer of which it is formed, the film is subjected to heat by heaing it to a temperature within the range between about 50° and 220° C. The structural modification of the film then takes place within the temperature range indicated, in each case within a relatively narrow temperature zone of less than 10° C., and proceeds spontaneously.
2. Subjecting the film to treatment with a gaseous or liquid medium which is capable of incipiently dissolving the plastic forming the film, for example, acetone in the form of liquid or vapor. The duration of the structural modification process depends on the concentration of the liquid medium and on its temperature. The structural modification takes place virtually spontaneously.

In accordance with the definition, the structural modification taing place virtually spontaneously is to be understood to mean that this modification is effected within an interval of seconds.

The structural modification of the film can also be effected by applying a compressive force to the latter.

Structural modification by the application of heat or a chemical medium to the film, as indicated above, can also be assisted by combining these measures of treatment in each case with the application of compressive force to the film.

In modifying the structure of the shaped article by subjecting the latter to the action of gaseous or liquid media which are capable of incipiently dissolving the plastic forming the shaped article, examples of suitable media of this type are tetrahydrofuran, low-molecular aliphatic alcohols, such as, for example, ethanol, and particularly acetone. The chemical media described are preferably applied in the form of vapor to the shaped article.

Depending on the intensity and/or the duration of action of the measures taken to modify the structure of the shaped articles, the structure of the latter can be modified to a greater or lesser extent, as required, in the limiting case until a virtually homogeneous physical stage is reached. Thus the permeability of an open-pore form of the shaped article according to the first variant can also be modified by the measures quoted only to the extent that a shaped article having pores of a smaller diameter and thus a higher selectivity is formed thereby. If temperature is used as a means of modification, the extent of the structural modification can be adjusted in a controlled manner, depending on the level of the temperature and the duration for which it acts. If the temperature acts for an adequate period, the structural modification takes place virtually completely, if it acts for a short period only a partial modification takes place.

If gaseous or liquid media are used for the structural modification, it is possible to control the modification of the structure by means of the concentration of these media and the period for which they act.

The structural modification of shaped articles according to the invention by the action of heat on the latter can be effected, for example, by subjecting them to the action of hot air at an adequate temperature or subjecting them to the action of infrared radiation. For example, a film composed of an indicated preferred copolymer in which one copolymerized component is copolymerized ethylene and which has a thickness of, for example, 30 μm, is subjected to a heat treatment by means of which it is heated to a temperature of approximately 90° C. The structural modification then takes place within a period of about 5 seconds.

It is also possible to prepare films which correspond in one or more segmentary regions to the somposition of the first variant of the invention, and correspond in one or more segmentary regions to the composition of the second variant of the invention. If this is intended, a film according to the first variant of the invention is subjected to one of the structural modification measures indicated only in a particular region.

It is also possible to modify, as indicated above, the structure of hollow fibers of a design according to the first variant of the subject of the inventon, by subjecting them to the action of, for example, heat or one of the chemical media described.

In the limiting case of complete modification of its structure, the shaped article according to the first variant of the subject of the invention appears virtually homogeneous physically and is thus transparent. The structure modification can in this case be carried out via intermediate stages of varying porosity and thus varying transmittance of light will the shaped article becomes transparent, up to the limiting case of virtually complete structural modification of the latter, by choosing the conditions under which this modification is carried out.

As the light transmittance of the shaped article increases, its free, light-refracting porosity decreases. Because it can be converted into a transparent state, the shaped article according to the first variant of the invention is described as having "latent transparency".

The pores of the shaped article according to the first variant of the subject of the invention can be charged with fluid, i.e., they can be filled up with the latter. By virtue of its composition, the structure of the shaped article remains stable when its pores are filled up with liquid and when this liquid is expelled again from the pores or allowed to evaporate from the latter at a later time.

In accordance with the definition, fluids are to be understood as meaning liquids to which the copolymer forming the shaped article according to the invention is resistant, so that the shaped article is practically not incipiently dissolved by these liquids. Fluids can be chemically single-substance liquids or solutions or mixtures of such liquids. Fluids can also be composed of liquids containing dissolved chemical substances. The solvent is then the carrier for the chemical active compound dissolved therein, which gets into the pores of the shaped article with, and by means of, this solvent when the shaped article is subjected to the action of the fluid and its pores are thereby filled up with this fluid.

Fluids can also be composed of liquids containing chemical active compounds in a dispersed or emulsified form. In this case, too, the continuous phase of the fluid is the carrier of the substance emulsified or dispersed therein. The liquid carrier causes the active compounds contained therein to reach the pores of the shaped article according to the invention, when the shaped article according to the invention, when the shaped article according to the first variant of the invention is subjected to the action of the fluids indicated.

An example of a fluid of the type first mentioned is an organic liquid-crystalline phase of 4-methoxy-benzylidene-4'-n-butylaniline (melting point 21° C.). An example of a fluid of the second type is a photosensitive sulfonamide of o-naphthoquinone diazide, dissolved in an organic phase (for example dodecane). An example of a fluid containing a dispersed or emulsified component of an active compound is an aqueous suspension of the thyroid hormone L-thyroxine.

Fluids can also contain, as the active compound, two or more chemically different substances, either dissolved, dispersed or emulsified.

In accordance with the definition, the term "fluids" is also intended, by extension, to embrace pastes and gels in which the liquid component thereof is the fluid in the narrower sense, since only this component penetrates into the pores of the film according to the invention when this film is subjected to the action of, or brought into contact with, the paste or gel. Examples of suitable gels are those based on agarose. They can have a water content of, for example, approximately 300%, relative to the weight of the gel-forming polymer. The aqueous fraction of the gel contains a dissolved chemical active compound, for example, scopolamine or nitroglycerin derivatives.

The pores of the shaped article can be charged with fluid by, for example, immersing this shaped article in a tank full of the fluid. After being taken out of the tank, the shaped article can be freed from excess fluid situated on its surface, for example, by being scraped, squeezed or wiped.

It is also possible to charge the pores of the shaped article with fluid only within segmentary regions of the latter. This will be illustrated by taking as an example a film according to the first variant of the invention. The procedure followed is as follows:

All the pores of the film are initially filled with fluid in the manner indicated above. The structure of the film is then modified within a segmentary region of the latter, for example, by allowing acetone vapor to act on the film. Fluid is contained in the film in an immobilized form within the structurally modified segmentary region of the film. It is advantageous to follow a procedure in which the film is charged overall with fluid and, before the structure-modifying measure, is covered with a mask corresponding in shape and dimensions to the film. The mask has openings of various shapes, for example, a grid composed of rectangular apertures. Acetone vapor is then allowed to act on the mask in such a way that the region of the film not covered by the mask is subjected to the action of the acetone. If saturated acetone vapor is used, the structural modification of the segmentary region of film which has been treated takes place within about 30 to 60 seconds.

The mask is then removed from the film and the fluid is eluted from the open pores of the film by means of a suitable liquid eluant. The fluid contained in the structurally modified segmentary regions of the film is not thereby eluted from the film.

The film is then treated in the manner indicated in order to refill its remaining pores with fluid. The fluid used in the second process stage differs chemically from that used in the first process stage. The structure of the film is then modified in the manner indicated above. The product then contains two fluids, differing chemically from one another, each in definite regions of the film, for example, in order to incorporate in a film two substances which are in themselves incompatible.

The process can also be carried out in such a way that, after the film has first been charged with fluid within segmentary regions of itself, the structural modification is carried out in such a way that the entire film is structurally modified. The product of the process is then a transparent film containing immobilized fluid within a discrete region.

If, for example, liquid, volatile aroma substances or solutions containing dissolved aroma substances are used as the fluid, or if liquid, volatile insecticides or solutions containing the latter are employed as the fluid, these fluids are temporarily immobilized in the film after it has been structurally modified. The chemical active compounds described emerge slowly by diffusion from the film which is virtually homogeneous physically, or from the segmentary regions thereof and, once outside the latter, they develop the desired action. This action has a long duration, corresponding to the rate of diffusion of the substances. If the fluid used is one which contains light-sensitive or heat-sensitive chemical compounds or reactive compounds which undergo a change in their structure or color under the action of an electric potential, a film according to the invention, which contains immobilized fluids of this type, can be used in the field of reproduction technology or can be employed for photographic processes. The color or the intensity of color of regions of film which appear virtually homogeneous physically and transparent as a result of structural modification in the manner indicated and which, if appropriate, contain immobilized fluid, corresponds to the color or intensity of color of the fluids contained in them or to the color-imparting chemical substances in these fluids.

The selectively permeable film according to the invention is thus not only characterized by an oleophilic-/oleophobic polymer structure, in terms of molecular distribution, which enables it to be used in a very wide variety of media—including corrosive media—and, for example, minimizes undesirable interactions (for example, the formation of a coating). By virtue of the polymer structure on which it is based, the selectively permeable film can, in addition, be adjusted in a controlled manner by the casting process as well as by subsequent modification of its structure, to have a very wide range of permeabilities over an extremely wide pore range from virtually homogeneous to effective pore diameters of 10 μm.

Further examplary uses of shaped articles according to the invention are indicated below and are in each case illustrated by taking as an example the use of a film according to the first variant of the invention.

1. The use of a film as a temporary depot and envelope for drugs, catalysts, enzymes, insecticides, dyestuffs, liquid crystals or corrosion inhibitors or for covering sterilized goods.

EXAMPLE

An aqueous, buffered suspension containing 50 mg of pilocarpine was poured into a bag made of 5 cm² of a film according to the invention, composed of copolymer (3), and the bag was tightly closed. The bag was then exposed for 30 seconds to a saturated atmosphere of acetone vapor. In the course thereof, the initially white film became opaque-translucent. This process was accompanied by a definite contraction of the pores and thus a desirable adjustment of their permeability. The bag was then introduced into 100 ml of a stirred buffer solution and was suspended in the latter. The kinetics of the release of the drug from the bag into the surrounding liquid were measured. After a start-up phase, the required constant zero order kinetics were established at a release rate of 16 mg of active compound per week.

2. The use of the film for analytical and diagnostic processes, such as immunodiffusion, immunoelectrophoresis, radioimmunoassay, agglutination tests and diagnostic test sticks.

EXAMPLE:

5 ml of an antigen solution of aqueous, buffered human albumin (8 μg) were introduced into a hole for the application of a sample in a copolymer film made of copolymer (5). The film had been applied in a layer thickness of 400 μm to a polyester film (Hostaphan 100 μm) and had previously been impregnated with a 14% strength antiserum for human albumin (rabbit). After a diffusion time of 24 hours in a humidity chamber, the layer was eluted for 48 hours in physiological NaCl solution and immediately afterwards was stained with a protein dyestuff (0.1 weight percent Coomassie Blue) and was fired for 60 seconds in acetone vapor. This resulted in a transparent film which had a distinctly pronounced radial precipitation zone and could be evaluated quantitatively by transmission.

3. Use as a reprographic and optical information carrier, for example, for photocopies using wet and dry toners (in particular for overhead projection), as a drawing film, as a substrate for reprographic films (in particular as a support for photoactive substances), as a thermopaper (for example, for thermocopiers), as a "mask" for retrieval of texts and optical information, for screening light-sensitive layers for a limited period (for example, film and photographic material), or conversely for exposing electro-optical or reactive systems for a limited period, for rendering visible for a definite period information, objects or rooms, or as an indicator of vapors and fluids and of specific temperatures.

(Example a)

A 50 μm thick white layer of a terpolymer film as specified in (4) or (3) on polyester film (Hostaphan 100 μm) was inscribed on an overhead projector with a felt pencil impregnated with dodecane. A presentation pattern which was transparent or reproduced the color of the film and which had sharp outlines was formed on a white substrate. After transmitting the desired information, this presentation pattern disappeared after a few minutes, so that the film could be used again.

(Example b)

A 30 μm thick white layer of terpolymer film as specified in (5) was subjected to wet toning in conformity with a technical test original on a photocopying machine (Infotec 1801) and was then fixed by heat at about 90° C. A scratchproof, transparent film was formed, which was distinguished by very high resolution power for the test lines and was suitable as an original for overhead projection.

4. Use as a membrane filter or ultra-filter for working-up (separating, concentrating or purifying) aerosols, dispersions, emulsions or dissolved or colloidal macromolecules in aqueous or gaseous systems, for example, for separating physiological liquids such as blood (hemofiltration, plasmapheresis and the like), milk or whey, or solutions from fermentative processes:

A membrane made of copolymer as specified in (3) was applied to a sheet of glass from a 20% strength polymer solution in dimethylacetamide by means of a doctor (slot height 150 μm) and was coagulated in water warmed to 40° C. After a dwell time of 15 minutes in the precipitation bath, the membrane was treated with 40% strength by weight of glycerol and was dried for 10 minutes at 100° C. The membrane, which was 60 μm thick, was stripped off the sheet of glass and its permeability at 1 bar was tested in a stirred test cell. Its volume flow with respect to water was 6,000 l/m²d, its retention capacity with respect to dispersed polyacrylate of diameter 0.2 μm (PLEXTOL, Rohm & Haas) was 100% and its retention capacity with respect to polyacrylic acid of 60,000 Daltons was 40%.

Since the films or tubular structures according to the invention can be welded, film bags or tubular bags can be prepared from them in a simple manner. This is done, for example, by placing two pieces of film, each of the same shape and dimensions, on top of one another in such a way that their edges are aligned. The pieces of film are then welded to one another in the region of their edges. In doing this, a bag open on one side is formed first, this bag is filled with material and is then closed in the manner indicated. If a piece of tube is used, this is first closed at one of its ends, its cavity is then filled with material, and the piece of tube is then also closed at the other end. Closure is effected in each case by welding.

The subject matter of the invention will be illustrated using FIGS. I and II as examples.

In FIG. I, a supporting film 1 is shown as a base layer upon which there is located a porous film 2 having an exposed surface 3. Reference numeral 4 denotes the interface between the porous film 3 and the supporting film 1.

In FIG. II, reference numeral 5 denotes a film having a virtually homogeneous physical structure, with 6 being its surface. The film 5 is shown in a state in which it is virtually stripped off from the plastic supporting film 7.

Within the scope of the description of the invention and the claims, the term "liquid film" or "liquid tubular structure" is intended to have the meaning "film composed of liquid" or "tubular structure composed of liquid", respectively.

What is claimed is:

1. A shaped article which is selectively permeable to liquids and gases, comprising a polymeric material which is comprised of at least 50% by weight of a copolymer comprising from about 20 to 80% by weight, relative to the total weight of the copolymer, of a copolymerized fluorinated olefin, from about 0 to 40% by weight, relative to the total weight of the copolymer, of a copolymerized olefin and from about 80 to 20% by weight, relative to the total weight of the copolymer, of copolymerized vinyl acetate, wherein at least about 5% by weight of the acetate groups in said copolymer relative to the total quantity thereof in the copolymer, have been converted into OH groups by saponification of said copolymer after the comonomers have been copolymerized to form the copolymer, and wherein the shaped article comprises a precipitation-induced selectively permeable, microporous, open-pore structure which is simultaneously olephilic and oleophobic.

2. A shaped article as claimed in claim 1, wherein said polymer comprises from about 30 to 70% by weight, relative to its total weight, of copolymerized tetrafluoroethylene, from about 0 to 20% by weight of copolymerized ethylene and from about 70 to 30% by weight, relative to the total weight of the copolymer, of copolymerized vinyl acetate.

3. A shaped article as claimed in claim 1, which comprises a film having effective pores of a diameter within the range from about 0.002 to 10 μm and through which liquids and gases can flow, and which has an inherent, latent capacity for modifying its structure until the limiting case of substantial physical homogeneity of the film is reached in response to chemical treatment, heat treatment or pressure application.

4. A shaped article as claimed in claim 1, which is in the shape of a hollow fiber having a wall which has effective pores of a diameter within the range from about 0.002 to 10 μm and through which liquids and gases can flow and which has an inherent, latent capacity for modifying its structure until the limiting case of substantial physical homogeneity of the wall has been reached in response to chemical treatment, heat treatment or pressure application.

5. A shaped article as claimed in claim 1, which comprises a film having effective pores of a diameter within the range from about 0.002 to 0.05 μm and through which liquids and gases can flow, and which has an inherent, latent capacity for modifying its structure until the limiting case of substantial physical homogeneity has been reached in response to chemical treatment, heat treatment or pressure application.

6. A shaped article as claimed in claim 1, which comprises a hollow fiber having a wall which has effective pores of a diameter within the range from about 0.002 to 0.05 μm and through which liquids and gases can flow, and which has an inherent, latent capacity for modifying its structure until the limiting case of substantial physical homogeneity of the wall has been reached in response to chemical treatment, heat treatment or pressure application.

7. A shaped article as claimed in claim 1, which comprises a film having effective pores of a diameter within the range from about 0.05 to 10 μm and through which liquids and gases can flow, and which has an inherent, latent capacity for modifying its structure until the limiting case of substantial physical homogeneity has been reached in response to chemical treatment, heat treatment or pressure application.

8. A shaped article as claimed in claim 1, which comprises a hollow fiber having a wall which has effective pores of a diameter within the range from about 0.05 to 10 μm and through which liquids and gases can flow, and which has an inherent, latent capacity for modifying its structure until the limiting case of substantial physical homogeneity of the wall has been reached in response to chemical treatment, heat treatment or pressure application.

9. A shaped article as claimed in claim 1, which has a substantially homogeneous physical structure, is permeable to liquids and gases by diffusion, and is transparent.

10. A shaped article as claimed in claim 9, which comprises a film.

11. A shaped article as claimed in claim 9, which comprises a hollow fiber.

12. A shaped article as claimed in claim 9, wherein the shaped article includes at least two segmentary regions, one of said regions comprising a microporous, open pore structure which is selectively permeable to liquids and gases, and the second of said regions comprising a substantially homogeneous physical structure which is transparent and permeable to liquids and gases by diffusion.

13. A shaped article as claimed in claim 1, wherein said fluorinated olefin comprises fluorinated ethylene or fluorinated propylene.

14. A shaped article as claimed in claim 12, wherein said fluorinated ethylene comprises perfluorinated ethylene.

15. A shaped article as claimed in claim 1, wherein at least about 80% by weight of the acetate groups have been converted into OH groups.

16. A shaped article as claimed in claim 1 produced by the process comprising the steps of:
preparing a copolymer comprising from about 20 to 80% by weight, relative to the total weight of the copolymer, of a copolymerized fluorinated olefin, from about 0 to 40% by weight, relative to the total weight of the copolymer, of a copolymerized olefin and from about 20 to 80% by weight, relative to the total weight of the copolymer, of copolymerized vinyl acetate;
saponifying at least 5% by weight of the acetate groups in the copolymer, relative to the total weight thereof in the copolymer, into OH groups after the comonomers have been copolymerized to form said copolymer;
providing said copolymer in a liquid solution;
forming a shaped article from said liquid solution; and
coagulating the copolymer by treating the shaped article with a precipitation liquid to form a shaped article having a microporous, open-pore structure and a stable shape.

17. A shaped article as claimed in claim 1, wherein the shaped article comprises at least two segmentary regions of different porosity.

18. A filtration device useful as an ultra-filter or hemo-filter or for separating or purifying dispersions, emulsions and dissolved macromolecules, comprising as a filtration membrane a shaped article as defined by claim 1.

19. A membrane filter useful for the separation of coarsely dispersed aqueous and gaseous systems, for separating particulate impurities from solutions for infusions, for separating cellular constituents from fermentation solutions, for separating bacteria or viruses from solutions or gases (sterile filters) or for separating very fine particles or aerosols from gases, comprising as the membrane filter a shaped article as defined by claim 1.

20. A reservoir containing low or high molecular-weight substances, comprising a shaped article according to claim 1.

21. A reservoir for containing low or high molecular-weight substances, comprising a shaped article according to claim 1, in the form of an envelope.

22. An information carrier, comprising a shaped article according to claim 1, being structurally converted in at least certain preselected areas, whereby the preselected areas represent information transferred by the shaped article.

23. A device for use in analytical and/or diagnostic processes, comprising a shaped article according to claim 1, for the separation of substances in gaseous and liquid phases and for the qualitative or quantitative evaluation of the separated substances.

24. A process for the preparation of a shaped article as claimed in claim 1, comprising the steps of:
providing a liquid solution which includes 1 to 50%, by total weight, of polymeric solute which comprises at least 50% by weight of a copolymer which is comprised of 20 to 80% by weight, relative to the total weight of the copolymer, of a copolymerized fluorinated olefin, from about 0 to 40% by weight, relative to its total weight, of a copolymerized olefin and from about 80 to 20% by weight, relative to its total weight, of copolymerized vinyl acetate;
saponifying at least 5% by weight of the acetate groups in the copolymer, relative to the total quantity thereof in the copolymer, into OH groups after the comonomers have been copolymerized to form said copolymer;
forming a shaped article from the liquid solution; and
coagulating the copolymer by treating the shaped article with a precipitation liquid to form a shaped article having a porous structure and a stable shape.

25. A process as claimed in claim 24, wherein a total of up to about 50% by weight of the polymer dissolved in the solution is comprised of one or more polymers which are miscible with one another and which differ in their qualitative chemical composition from said copolymer, the polymers being selected from a group comprising polyvinylidene fluoride, a polar polyolefin, silicones and a mixture of these polymers.

26. A process as claimed in claim 24, wherein the polymer solution comprises, as the dissolved component, from about 1 to 50% by weight, relative to the total weight of the solution, of a copolymer which is comprised of from about 30 to 70% by weight, relative to its total weight, of copolymerized tetrafluoroethylene, from about 0 to 20% by weight, relative to its total weight, of copolymerized ethylene and from about 70 to 30% by weight, relative to its total weight, of copolymerized vinyl acetate.

27. A process as claimed in claim 24, wherein the copolymer is crosslinked with other similar copolymer units produced according to the present invention, with a mixture of polymers or with at least one multifunctional agent.

28. A process as claimed in claim 24, wherein the shaped article comprises a flat film.

29. A process as claimed in claim 24, wherein the shaped article comprises a hollow fiber.

30. A process as claimed in claim 24, wherein said fluorinated olefin comprises fluorinated ethylene or fluorinated propylene.

31. A process as claimed in claim 30, wherein said fluorinated olefin comprises perfluorinated ethylene.

32. A process as claimed in claim 24, wherein said saponifying step converts at least about 80% by weight of the acetate groups into OH groups.

33. A process for modifying the structure of a shaped article as claimed in claim 1, comprising the steps of:
subjecting a shaped article to the action of a chemical agent which is capable of rendering the structure of the copolymer of which the shaped article is formed physically or optically homogeneous.

34. A process as claimed in claim 33, wherein the shaped article is subjected to the action of a chemical medium in the form of vapor.

35. A process for modifying the structure of a shaped article as claimed in claim 1, comprising the steps of:
subjecting a shaped article to heat treatment which is capable of rendering the structure of the copolymer of which the shaped article is formed physically or optically homogeneous.

* * * * *